United States Patent [19]

Khuri-Yakub et al.

[11] Patent Number: 5,383,369
[45] Date of Patent: Jan. 24, 1995

[54] DEVICE FOR MEASURING THE VELOCITY OF A FLUID

[75] Inventors: Butrus Khuri-Yakub, Palo Alto, Calif.; Patrice Ligneul, Chaville; Jean-Luc Boulanger, Montrouge, all of France

[73] Assignee: Schlumberger Industries, Montrouge, France

[21] Appl. No.: 231,864

[22] Filed: Apr. 25, 1994

Related U.S. Application Data

[63] Continuation of Ser. No. 961,585, Oct. 15, 1992, abandoned.

[30] Foreign Application Priority Data

Oct. 25, 1991 [FR] France ............... 91 13299

[51] Int. Cl.⁶ .............................................. G01F 1/00
[52] U.S. Cl. ................................. 73/861.29; 73/571
[58] Field of Search ............ 73/170.02, 170.03, 170.11, 73/170.13, 861.22, 861.23, 861.27, 861.28, 861.29, 170.34, 571, 586, 591

[56] References Cited

U.S. PATENT DOCUMENTS 3,729,993  5/1973  Eck et al.
4,555,951  12/1985  Gutterman

FOREIGN PATENT DOCUMENTS

WOA8602723  5/1986  WIPO
WOA9114925  10/1991  WIPO

Primary Examiner—Richard E. Chilcot, Jr.
Assistant Examiner—R. Biegel
Attorney, Agent, or Firm—Sanford J. Asman

[57] ABSTRACT

To avoid disturbing measurement dephasings due to reflections from walls, the fluid velocity-measurement device comprises a pair of input-output transducers (18 and 20) located inside measurement chamber (16) which has the form of a revolution ellipsoid, each of transducers (18 and 20) being mounted at one of the focal points (F1 and F2) of the ellipsoid.

16 Claims, 2 Drawing Sheets

DEVICE FOR MEASURING THE VELOCITY OF A FLUID

This application is a continuation of application Ser. No. 07/961,585, filed on Oct. 15, 1992, entitled DEVICE FOR MEASURING THE VELOCITY OF A FLUID, now abandoned.

The present Invention concerns a device for measuring the velocity of a fluid. This is a static device, operating without any moving mechanical parts. It is suitable particularly for use in static gas meters.

BACKGROUND OF THE INVENTION

A description of a device for measuring the velocity of a fluid is available in document EP 0 347 096. In this known device, a measurement is taken of the time required for an acoustical signal to travel between two input-output transducers located at the ends of a cylinder through which the fluid is flowing.

If the distance between the two transducers is known, then the time taken for an acoustical signal to travel between the first transducer and the second, and between the second transducer back to the first, allows determining the velocity of the gas in the pipe.

However, this device has several disadvantages. The acoustical waves are emitted by the transducers with a conical radiation pattern. Apart from those waves actually on or near the centerline of the pipe, the waves are reflected off the pipe walls before reaching a receiver. These reflections lead to differences in the signal paths, hence to dephasing, depending on the transmission angle. Dephasing can lead to destructive interference at the receiver, which markedly decreases the intensity of the detected signal.

In addition, the radiation pattern implies increasing the frontal surface of the transmitter-receivers in order to increase the volume of signal received.

Finally, it follows that the electrical source required for supplying the transmitter-receivers must be powerful, which precludes the standard solution of an electric cell suitable for long periods of operation.

Notwithstanding, for use in a domestic gas meter, the device must be able to operate with very low electrical consumption, hence be compatible with such standard battery supplies, guaranteeing a service life of several years.

SUMMARY OF THE INVENTION

The purpose of the present Invention is to obviate the disadvantages of known devices. Through the use of a revolution-ellipsoid chamber, all of the ultrasonic waves emitted and received by the transducers located at the focal points of the ellipsoid are reflected off the walls of the latter and reach the distant focal point after travelling over the same distance, hence without any dephasing liable to diminish the detected intensity.

There exists nevertheless a certain degree of dephasing between waves emitted quasi-axially (Which reach the distant receiver without any reflection off a wall) and those waves that are reflected off a wall. This dephasing phenomenon can be rendered negligible or non-detrimental to the detected signal by suitable shaping of the ellipsoid.

It is also possible to inhibit quasi-axial waves by placing an obstacle in their path.

In addition, the signal volume received by each receiver is greater than with the previous technology since the reflected waves are directed in totality to the focal points of the ellipsoids where the transmitter-receivers are located (except for, naturally, waves escaping through the measurement-chamber openings necessary for passage of the fluid).

In these conditions, it is possible to employ transmitter-receivers of smaller dimensions than required by the previous technology, which means they can be installed in the gas stream without disrupting the latter to any significant extent.

In more precise terms, the present Invention concerns a device for measuring the velocity of a fluid, comprising a pair of ultrasonic transducers (input and/or output transducers) and a measurement chamber in the form of a revolution ellipsoid, with one exit opening and one outlet opening and an ultrasound-reflecting wall, each of the input-output transducers being positioned at one of the focal points of the ellipsoid.

In one version, the ellipsoid is such that the sum of the distances from a point on the ellipsoid to the focal points, minus the distance between the focal points, is practically equal to a multiple integer of the ultrasonic wave length.

In one version, the intake and outlet of the measurement chamber are aligned with the major axis of the ellipsoid.

Advantageously, the device comprises an intake chamber with the form of a converging nozzle, connected to one intake of the measurement chamber.

Advantageously, the device comprises an outlet chamber in the form of a diverging nozzle, connected to one outlet of the measurement chamber.

Advantageously, the measurement chamber has an obstacle fitted longitudinally on the major axis of the ellipsoid in order to produce a practically constant transverse distribution of the fluid velocity crossing the chamber, irrespective of the flow rate inside the measurement chamber.

Advantageously, this obstacle has an aerodynamic shape with cylindrical symmetry about the major axis of the ellipsoid.

In preferred terms, the obstacle has an ogival shape, with an ellipsoidal longitudinal section such that the distance between the wall of the measurement chamber and the major part of the surface of the obstacle is constant.

In one version, the ogive has a tapered end opposite the intake opening. In addition to its enabling a practically constant transverse fluid velocity, such an obstacle reduces flow-separation turbulence phenomena in the measurement chamber, and thus reduces load losses.

The obstacle also increases the fluid velocity through the chamber, and thus increases the sensitivity of the device.

In preferred terms, the obstacle is positioned to mask at least each transducer to ultrasonic waves transmitted quasi-axially by the distant transducer.

Thus the problem of ultrasonic waves reaching the receiving transducer without being reflected off the measurement-chamber wall is avoided. Additionally, this eliminates any interference occurring between ultrasonic waves propagating directly from one transducer to the other, and those reflected off the wall of the measurement chamber.

Advantageously, the obstacle is maintained in position by a support comprising a series of shaped vanes integral at one end with one wall of the measurement chamber and at the other end with the obstacle.

In one variant of the device conforming to the Invention, the transducers are maintained in position by supports which also act as flow vanes streamlining the fluid flow.

Preferentially for this variant, the flow vanes comprise several equidistant surfaces set perpendicular to the major axis of the ellipsoid and mounted to the wall of the measurement chamber.

Advantageously, the transducers are placed in aerodynamically shaped modules.

Advantageously, the minor axis of the ellipsoid is practically equal to the diameter of the pipe through which the fluid is flowing.

Preferentially, the inter-focal-point distance lies in a range of between four and six times the diameter of the pipe through which the fluid is flowing.

BRIEF DESCRIPTION OF THE DRAWINGS

The characteristics and advantages of the Invention will be better appreciated by reading the following description—which is provided for reference purposes and is not exhaustive—in unison with the attached figures in which.

DESCRIPTION OF THE PREFERRED EMBODIMENTS

With reference to FIG. 1, the following is a description of a device conforming to the Invention, connected to cylindrical intake pipe 10 in which the fluid (for example, a gas) is flowing, and an outlet pipe 12, also cylindrical. Pipes 10 and 12 have a diameter of "D".

Figure 1A:
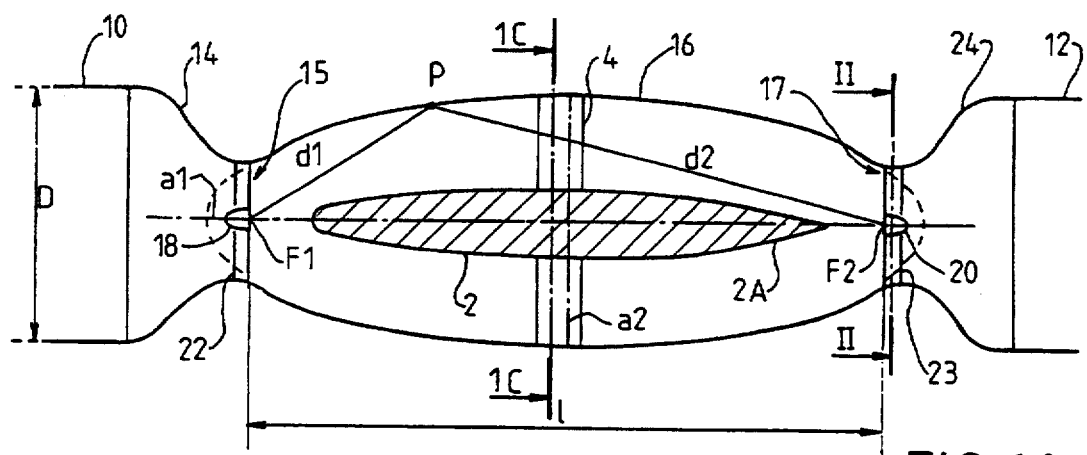
FIG. 1A is a schematic representation of a longitudinal section of a device conforming to the Invention.

In the version represented by FIG. 1A, the device described by the Invention comprises a cylindrical intake chamber 14 having the form of a converging nozzle and an intake diameter equal to "D", and an outlet diameter equal, for example, to D/2. The intake chamber is connected at its widest diameter to intake pipe 10, and at its smallest diameter to measurement chamber 16.

Measurement chamber 16 has an ellipsoid shape with a major axis a1 and a minor axis a2. Intake 15 and outlet 17 of measurement chamber 16 are aligned with major axis a1. Optimally, minor axis a2 is equal to diameter "D" of the intake pipe.

The ellipsoid is chosen such that inter-focal-point distance (I) lies in a range of between four and six times "D"; for example, (I) is selected as equal to 5D.

Measurement chamber 16 has an internal wall capable of reflecting ultrasounds.

Two input-output transducers 18 and 20 are positioned at the focal points of the ellipsoid, (F1) and (F2), with their active surfaces facing each other.

Transducers 18 and 20 are made, for example, from piezoelectric ceramic (PZT, for example) and comprise an impedance-matching layer (for example, RTV rubber).

Transducers 18 and 20 have a diameter of approximately (0.1)D. Placed in the fluid stream, they create a minimum amount of flow disturbance thanks to their compact size. In order further to reduce disturbance, transducers 18 and 20 are set in aerodynamically shaped modules.

Transducers 18 and 20 are maintained in position by supports 22 and 23 fixed to the wall of measurement chamber 16 in the example represented in FIG. 1A.

In the example described and represented in FIG. 1A, supports 22 and 23 also have a streamlining function for the fluid, that is, they serve to suppress turbulence phenomena in the fluid and equalize velocity distribution transverse to the fluid flow.

Figure 2:
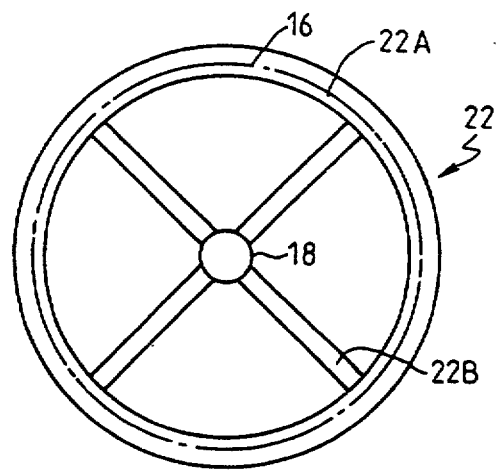
FIG. 2 is a schematic representation of a transverse section taken along axis II in FIG. 1 of the device conforming to the Invention.

FIG. 2 represents a cross-section along axis II in FIG. 1A. It can be seen that support 22 comprises ring 22A fixed to the inner wall of measurement chamber 16. Four radial fins 22B spaced equidistant around the circumference of ring 22A meet in the center to form a support for transducer 18.

Support 23 is identical to support 22. It can be seen in FIG. 1A that outlet 17 of measurement chamber 16 is connected to outlet chamber 24 which has the form of a diverging nozzle. Outlet chamber 24 is connected to outlet pipe 12.

Measurement chamber 16 has an obstacle 2 fitted longitudinally along the major axis (axis a1) of the ellipsoid, in order to produce a practically constant transverse velocity distribution in the fluid crossing the chamber, irrespective of the flow rate inside the measurement chamber. This obstacle can consist of an ultrasound-absorptive material, such as polyurethane, or any equivalent material. In this way, spurious wave-reflections on the obstacle itself are avoided.

Obstacle 2 has an aerodynamic shape with cylindrical symmetry about major axis a1 of the ellipsoid. As can be seen in FIG. 1A, the obstacle has an ogival shape, with an ellipsoidal longitudinal section such that the distance between the wall of measurement chamber 16 and the major part of the surface of obstacle 2 is constant. In the version depicted in FIG. 1A, the ogive has a tapered end 2A opposite intake opening 15.

Figure 1C:
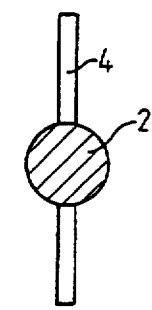
FIG. 1C is a schematic representation of a transverse section taken along axis 1C in FIG. 1 of the device conforming to the Invention.
Figure 1B:
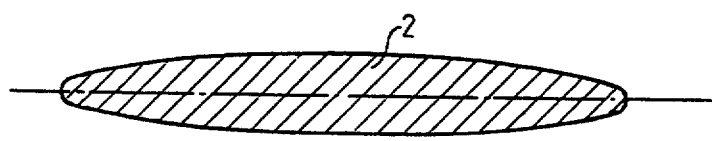
FIG. 1B is a schematic representation of one version of an obstacle placed in the measurement chamber.

FIG. 1B is a schematic representation of a longitudinal cross-section of obstacle 2 in one variant; it can be seen that the obstacle may be completely ellipsoidal, that is, symmetrical about its minor axis.

Obstacle 2 is maintained in position by support 4 comprising a series of shaped vanes integral at one end with one wall of chamber 16 and at the other end with obstacle 2.

FIG. 1C is a schematic representation of a transverse cross-section taken along axis 1C, showing a front view of the assembly comprising obstacle 2 and support 4.

The shaped blades, which are two in number in FIG. 1C but can be any number, fulfil a streamlining function for fluid traversing chamber 16.

Again in FIG. A1, it will be seen that obstacle 2 is arranged so as to mask ultrasonic waves emitted by either of transducers 18 or 20 and propagating quasi-axially. This eliminates any direct propagation between one transducer and another, the only useful waves being those undergoing reflection on the wall of chamber 16.

In operation, the fluid travels through the device from intake pipe 10 towards outlet pipe 12.

Passage of fluid through intake chamber 14, which has the shape of a converging nozzle, enables the fluid velocity to be increased by a known quantity in relation to the initial velocity. In this way, the quality of the flow is also improved.

Obstacle 2 allows obtaining a constant transverse velocity profile, irrespective of the fluid velocity; the quality of the flow is further enhanced by the flow vanes.

Each of transducers 18 and 20 emits an ultrasonic wave with a frequency in the 0.2 to 1 MHz range, towards the opposite transducer. The frontal emitting surfaces are located at F1 and F2, the focal points of the ellipsoid. It is a known fact that the sum of distances d1 and d2 from the focal points to any point P on the ellipsoid is a constant.

Since the transducer emission has a conical pattern, all waves reflected off the wall of the ellipsoid before reaching the opposite transducer will travel the same distance.

Waves emitted quasi-axially with major axis a1 of the ellipsoid do not undergo reflection before reaching the opposite transducer. For this reason, there exists a certain degree of dephasing between these waves and those waves that are reflected off the ellipsoid wall. Nevertheless, this dephasing phenomenon can be controlled to prevent any creation of destructive interference. The dephasing value depends on the parameters of the ellipsoid: the latter is thus selected so that the sum of distances d1 and d2, less inter-focal-point distance (I), is roughly equal to a multiple integer of the ultrasonic wave length.

It is known that the wave length depends on the speed of sound, and frequency. If operating conditions vary, the speed of sound, and hence the wave length, will also vary. It is possible to adjust the frequency to allow for changes in speed of sound, and still provide a multiple integer value for the wave length. For this, any known frequency-variation technique may be employed, such as the lambda locked loop.

Nevertheless, if, as in the example represented in FIG. 1A, chamber 16 comprises an obstacle 2 that prevents any axial propagation of ultrasonic waves, the need to respect this condition no longer applies.

The velocity of the gas inside the measurement chamber is a function of distance (I) between the focal points, and the durations required for a wave emitted by one transducer to reach the other transducer, both in the direction of fluid propagation and in the reverse direction. This velocity is determined by a method practically identical to that employed in the previous technology.

Using the geometrical characteristics of measurement chamber 16 and the value obtained from determination of the velocity of flow, it is possible to estimate the flow rate.

Figure 3:
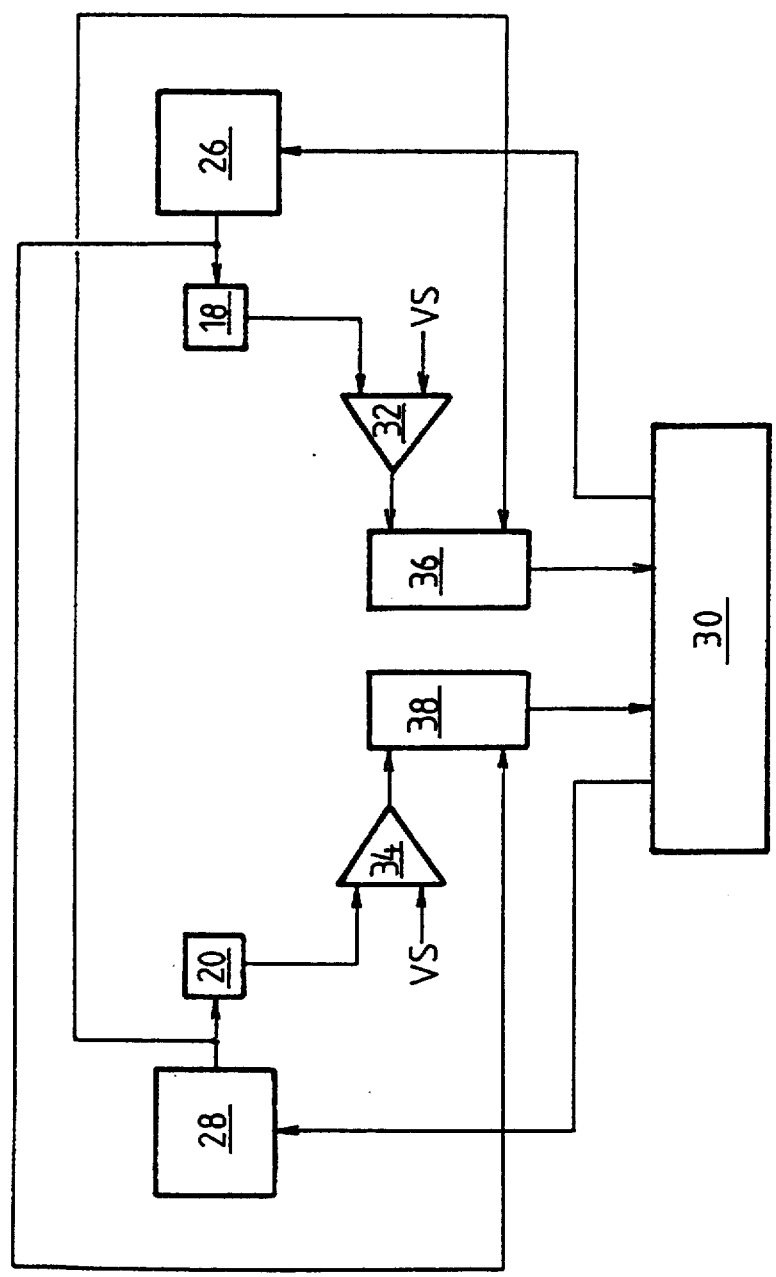
FIG. 3 is a schematic representation of an electronic assembly enabling determination of fluid velocity using measurements performed by a device conforming to the Invention.

FIG. 3 is a schematic representation of an electronic assembly enabling determination of the fluid velocity. Several known processes can be used to determine fluid velocity: phase measurement, time of flight, or frequency measurement using looped transducers in an oscillator circuit, and so on. The following description concerns a baseline circuit for measuring time of flight. Transducers 18 and 20 are connected respectively to impulse generators 26 and 28 subjected to alternating control from, for example, a microprocessor 30 equipped with the usual peripherals.

Each of transducers 18 and 20 is connected to a threshold amplifier, 32 and 34 respectively; the amplifier trigger threshold (VS) is determined according to the operating conditions. Threshold amplifiers 32 and 34 are connected to counters 36 and 38 respectively. The counter outputs are connected to a calculation device, such as microprocessor 30.

Under the control of microprocessor 30, transducer 18 is excited during the pulse created by pulse generator 26. It thus delivers an ultrasonic pulse towards transducer 20. In addition, pulse generator 26 is connected to one input of counter 38, which is triggered as the pulse is emitted.

When transducer 20 receives the ultrasonic pulse from transducer 18, it delivers an electrical signal to the input of threshold amplifier 34. When the signal from transducer 20 exceeds threshold VS, amplifier 34 delivers an electrical signal to one input of counter 38, which stops counting. Microprocessor 30, connected to the output of counter 38 then determines the time of flight of one ultrasonic pulse between transducer 18 and transducer 20.

Once the above operation is complete, a similar operation is triggered for transducer 20, which emits an ultrasonic pulse detected by transducer 18.

By measuring the passage time in the opposite direction, the microprocessor can determine the velocity of the fluid flow, since all other parameters are known (in particular, the geometrical characteristics of the ellipsoid).

We claim:

1. A device for measuring the velocity of a fluid travelling through a pipe (10), comprising a flow conduit having a first ultrasonic transducer (18) and a second ultrasonic transducer (20) and a measurement chamber (16), in which the measurement chamber (16) is shaped as a revolution ellipsoid having first and second focal points along an ellipsoidal major axis which is able to reflect ultrasound, said first transducer being located at said first focal point (F1) and said second transducer being located at said second focal point (F2) of the ellipsoid.

2. The device of claim 1 in which the ellipsoid is such that the sum of distances (d1 and d2) from a point (P) on the ellipsoid to said focal points (F1 and F2), minus the distance (1) between said focal points (F1 and F2), is substantially equal to a multiple integer of the ultrasonic wave length.

3. The device of claim 1, in which the measurement chamber (16) has an intake (15) and an outlet (17) aligned with ellipsoid major axis (a1).

4. The device of claim 1 further comprising an intake chamber (14) having the shape of a converging nozzle which is connected to said measurement chamber (16).

5. The device of claim 1 further comprising an outlet chamber (24) having the shape of a diverging nozzle which is connected to said measurement chamber (16).

6. The device of claim 1 in which the measurement chamber (16) contains obstacle (2) positioned longitudinally along ellipsoid major axis (a1) in order to produce a substantially constant transverse velocity distribution in the fluid crossing measurement chamber (16), irrespective of the flow rate inside measurement chamber (16).

7. The device of claim 1, in which the obstacle (2) has an aerodynamic shape with cylindrical symmetry about major axis a1 of the ellipsoid.

8. The device of claim 7, in which the obstacle (2) has an ogive shape with with an ellipsoidal longitudinal section such that the distance between the wall of measurement chamber (16) and the major part of the surface of obstacle (2) is constant.

9. The device of claim 8, in which the ogive has a tapered end opposite intake opening (15).

10. The device of claim 1, in which the obstacle (2) is positioned so as to mask at least each of transducers (18 and 20) to ultrasonic waves transmitted quasi-axially by the distant transducer.

11. The device of claim 1, in which the obstacle (2) is maintained in position in measurement chamber (16) by support (4) comprising a series of shaped vanes integral at one end with one wall of measurement chamber (16) and at the other end with obstacle (2).

12. The device of claim 1 further comprising a first support for supporting said first transducer and a second support for supporting said second transducer, said supports having a shape whereby they also act as flow vanes for streamlining the fluid flow.

13. The device of claim 12, in which the flow vanes comprise several equidistant surfaces set perpendicular to the ellipsoid major axis (a1) and mounted to the wall of measurement chamber (16).

14. The device of claim 1 in which each of said transducers (18 and 20) is placed in an aerodynamically shaped module.

15. The device of claim 1 in which the ellipsoid minor axis (a2) is substantially equal to the diameter (D) of a pipe (10) through which the fluid is flowing.

16. The device of claim 1, in which the inter-focal-point distance (1) lies in a range of between four and six times the diameter (D) of pipe (10) through which the fluid is flowing.

* * * * *